US00PP37254P2

(12) United States Plant Patent
Meulenbroek

(10) Patent No.: US PP37,254 P2
(45) Date of Patent: Feb. 10, 2026

(54) STRAWBERRY PLANT NAMED 'BACHATA'

(50) Latin Name: *Fragaria x ananassa (Duch.)*
Varietal Denomination: BACHATA

(71) Applicant: Fresh Forward Holding B.V., Huissen (NL)

(72) Inventor: Bert Meulenbroek, Zetten (NL)

(73) Assignee: Fresh Forward Holding B.V., Huissen (NL)

( * ) Notice: Subject to any disclaimer, the term of this patent is extended or adjusted under 35 U.S.C. 154(b) by 0 days.

(21) Appl. No.: 19/194,236

(22) Filed: Apr. 30, 2025

(51) Int. Cl.
*A01H 5/08* (2018.01)

(52) U.S. Cl.
USPC ..... Plt./208

(58) Field of Classification Search
USPC ..... Plt./208
CPC ..... A01H 6/7409; A01H 5/08
See application file for complete search history.

*Primary Examiner* — Keith O. Robinson
(74) *Attorney, Agent, or Firm* — The Webb Law Firm

(57) ABSTRACT

A new and distinct strawberry plant is provided which exhibits strong to medium vigor, with fruit having an ovoid to rhomboid shape, and medium red color.

5 Drawing Sheets

Botanical classification: *Fragaria x ananassa* (*Duch.*).
Varietal denomination: 'BACHATA'.

BACKGROUND OF THE INVENTION

The present invention comprises a new and distinct variety of strawberry plant botanically classified as *Fragaria* x *ananassa* (Duch.) and known by the varietal name 'BACHATA'. The new variety is the result of cross-pollination between strawberry plants referred to as 'MERCED' (female parent, U.S. Plant Pat. No. 25,436) and 'FANDANGO', previously known as 'FS 1705' (male parent, U.S. Plant Pat. No. 32,667) during the spring in 2016 in Eck en Wiel, The Netherlands. Selection was carried out on the breeding premises of the applicant in Huelva, Spain in April 2018. The purpose of breeding program was to create a high quality, productive and early ripening variety suitable for the Mediterranean production region. Subsequently, the new variety was asexually reproduced by runners in 2018 in Eck en Wiel, The Netherlands. The new variety has been trial and field tested and has been found to retain its distinctive characteristics and remain true to type through successive asexual propagations. The new variety has not been evaluated under all possible environmental conditions. The phenotype may vary with variations in environment without a change in the genotype of the plant.

The new variety is similar to its female parent in having sunken seeds and a crenate terminal leaflet margin; however, 'BACHATA' differs from its female parent in the position of calyx attachment (raised versus flat or inserted for 'MERCED'). The new variety is similar to its male parent in the position of calyx attachment (raised); however, 'BACHATA' differs from its male parent in the fruit color (RHS 44A versus RHS 40A for 'FANDANGO').

When compared to strawberry variety named 'ROCIERA FNM' (unpatented, but described in Community Plant Variety Rights Application No. 20151915), 'BACHATA' exhibits a semi-upright growth habit (versus upright for 'ROCIERA FNM'), medium density of foliage (versus dense for 'ROCIERA FNM'), an ovoid fruit shape (versus conical for 'ROCIERA FNM'), a raised position of calyx attachment (versus level with the fruit for 'ROCIERA FNM'), and an upward attitude of sepals (versus an outward attitude for 'ROCIERA FNM').

The following characteristics also distinguish the new variety from other strawberry varieties known to the breeder:

Fruit: shape ovoid to rhomboid
Fruit: color medium red
Plant: vigor strong to medium
Leaf: color of upper side dark green
Fruit: position of achenes (strongly) below surface
Fruit: position of calyx attachment raised

DESCRIPTION OF THE DRAWINGS

The accompanying photographic drawings illustrate the new variety at approximately 3-4 months after planting, with the color being as nearly true as is possible with color illustrations of this type. It should be noted that colors may vary with growing conditions and time of year.

DESCRIPTION OF THE PLANT

Figure 1:
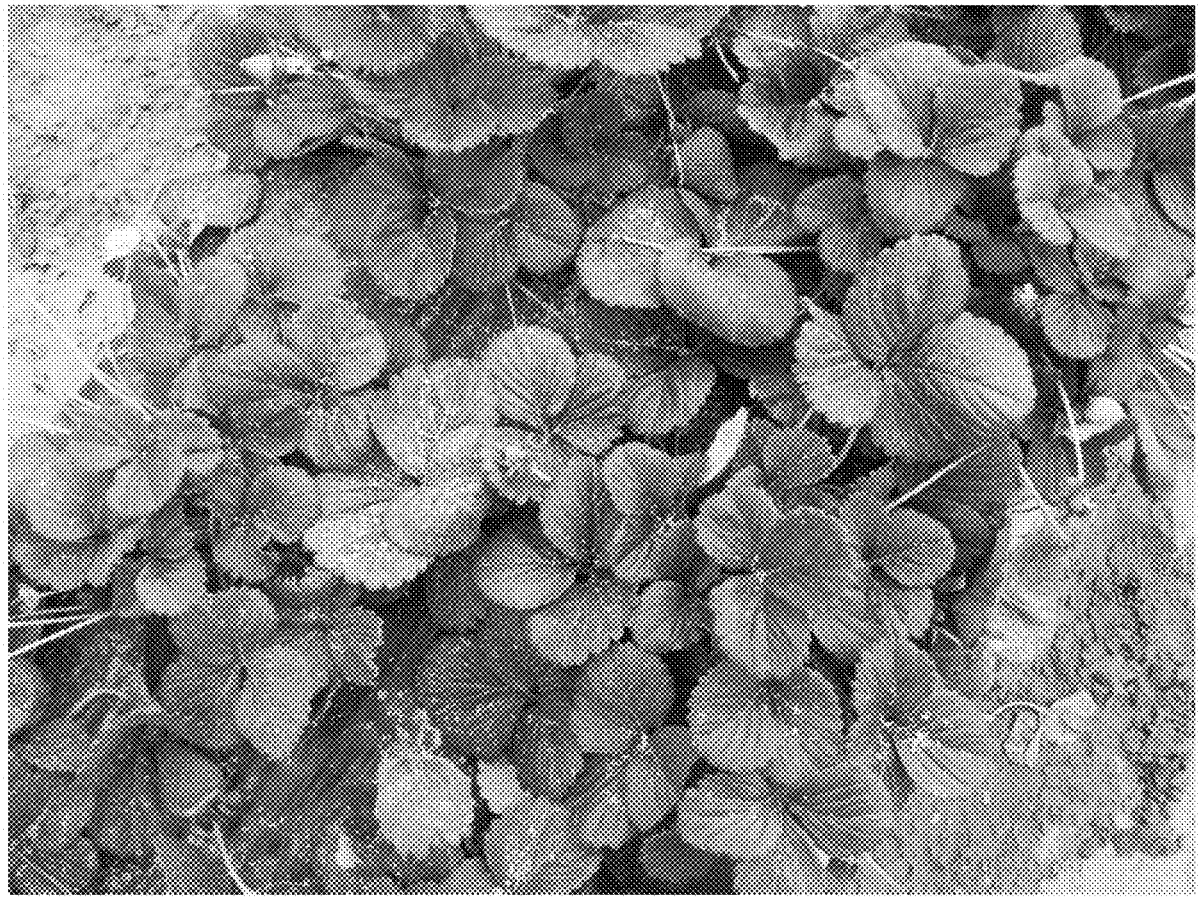
FIG. 1 is a photograph of an entire plant the new variety.
Figure 2:
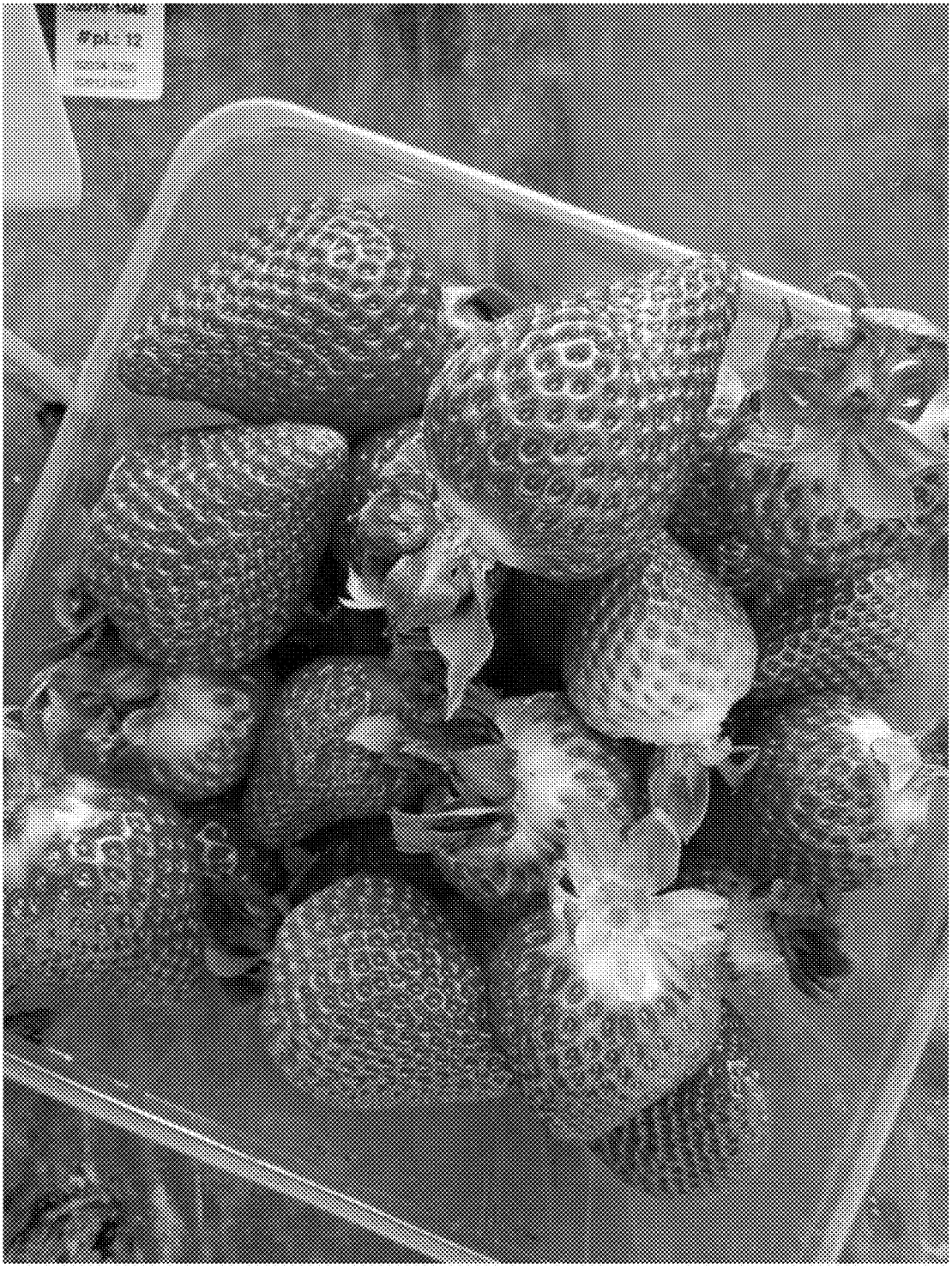
FIG. 2 is a photograph of whole fruits of the new variety.
Figure 3:
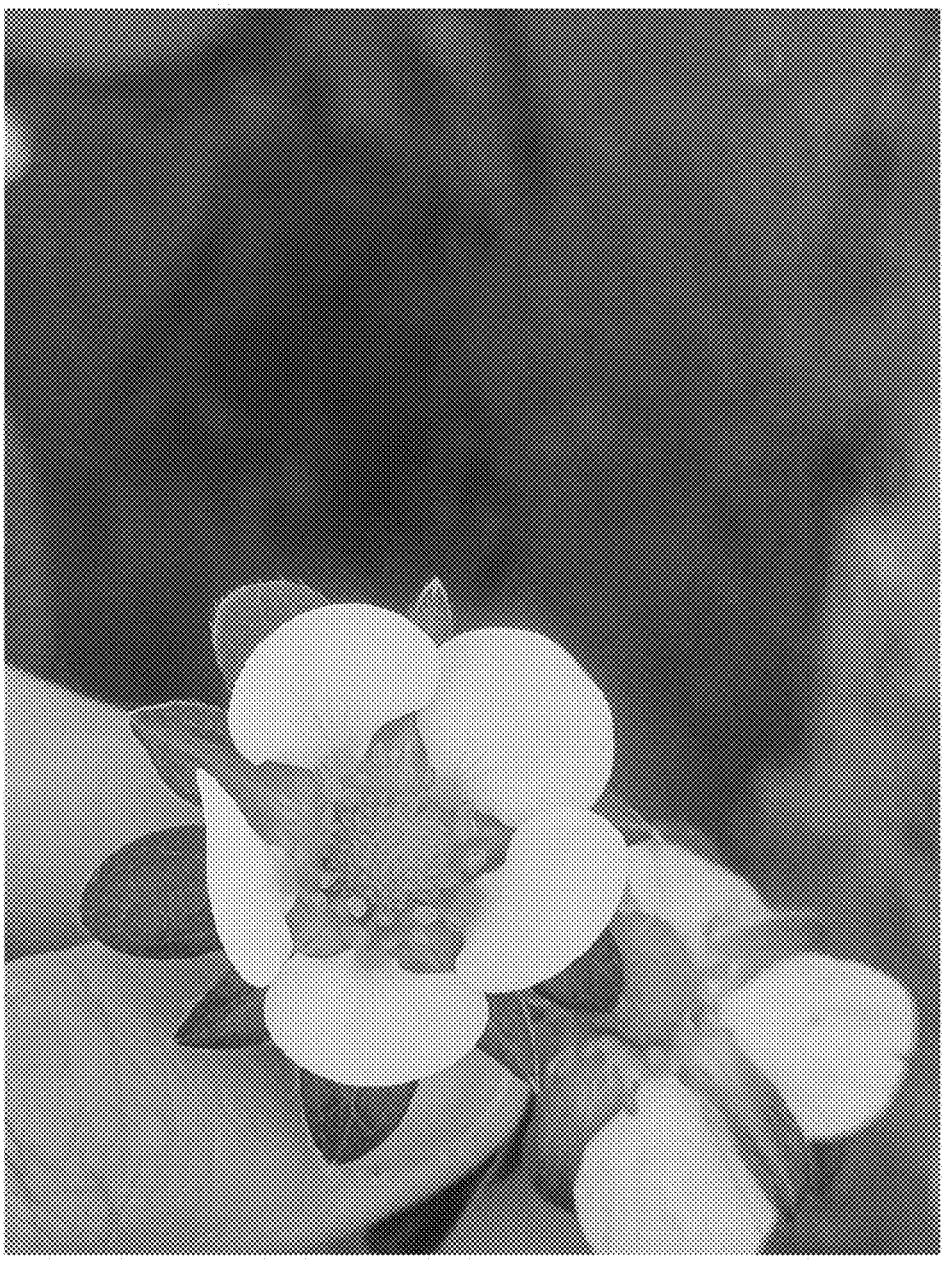
FIG. 3 is a photograph of a flower of the new variety.
Figure 4:
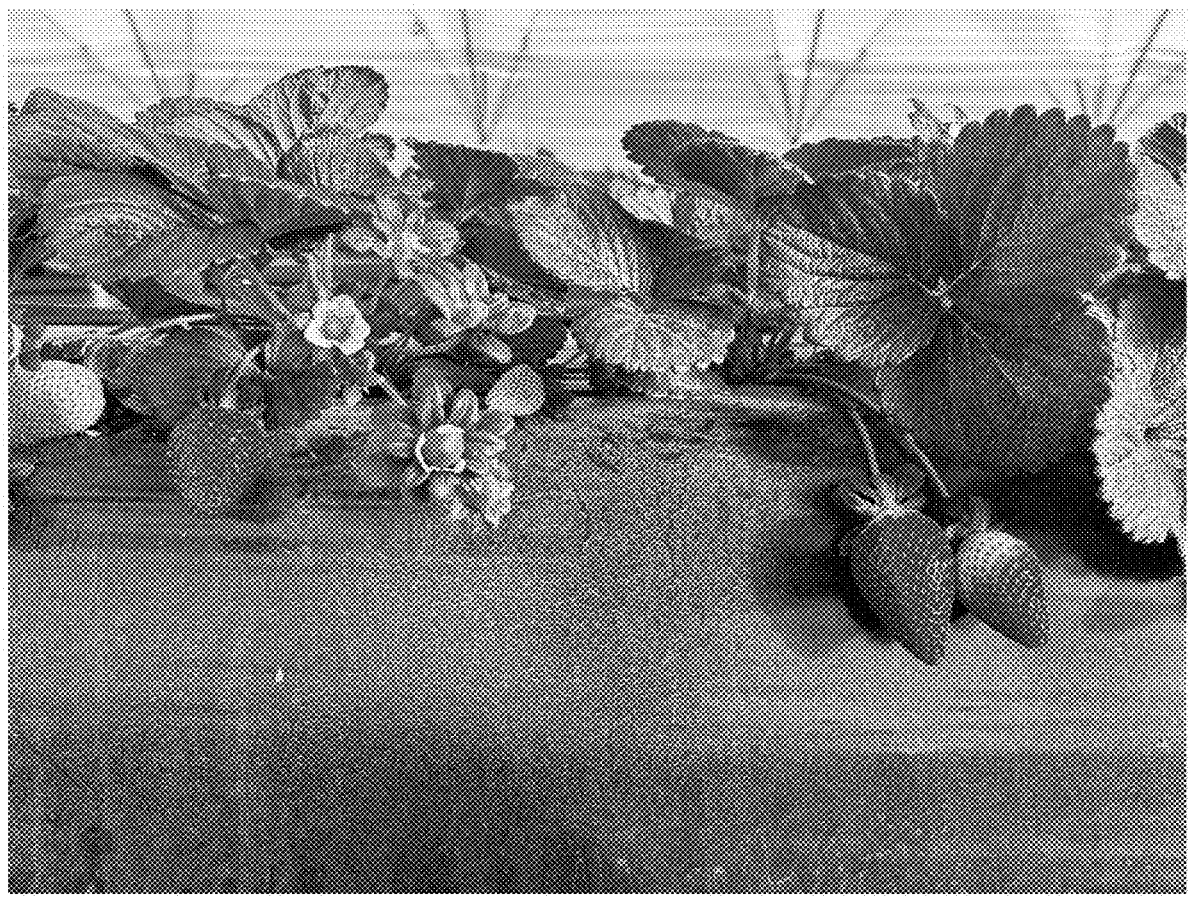
FIG. 4 is a photograph of an entire plant the new variety.
Figure 5:
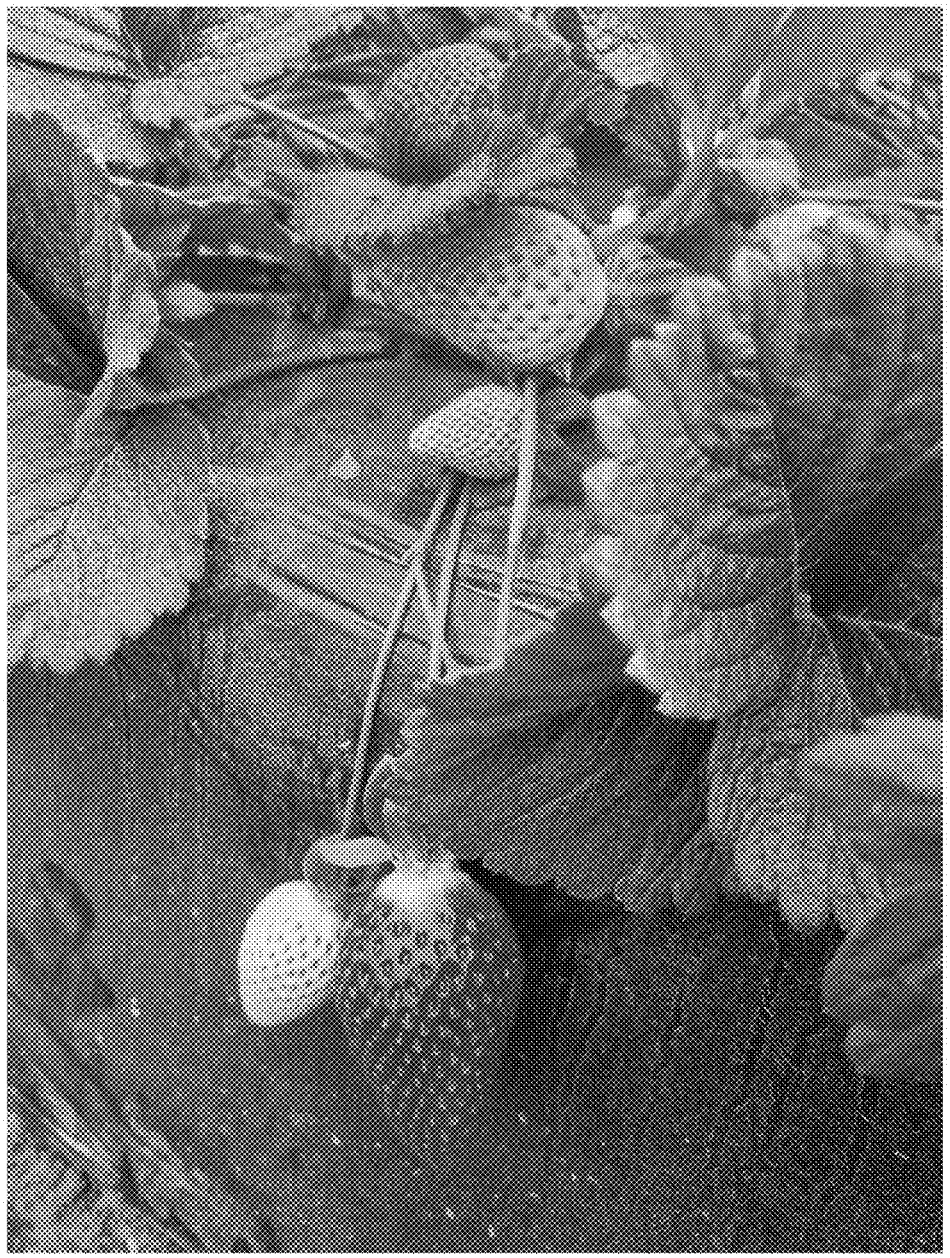
FIG. 5 is a photograph of whole fruits of the new variety.

The following detailed description sets forth the characteristics of the new cultivar. The new variety was grown under natural light conditions in Rociana del Condado, Spain, with an average day temperature of 20° C. and an average night temperature of 12° C. The new variety was approximately 3-4 months of age when described. Color references are primarily to the Sixth Edition (2015) of The R.H.S. Colour Chart of The Royal Horticultural Society of London and were identified under natural light.

PLANT

Time to initiate roots: 4 days at an average temperature of 15-22° C.

Time to produce a rooted plant: 30 days at an average temperature of 15-22° C.

Time to produce a finished plant: 2 months at 12-22° C.

Rooting habit: Traditional.

Form (e.g., spreading, mounded, symmetrical, etc.): Semi-upright to upright.

Height (from soil to top of plant): Approximately 15 cm.

Plant diameter: Approximately 30 cm.

Vigor: Medium to strong.

Disease/pest resistance or tolerance: Reasonable resistant to mildew (*Podosphaera macularis*) and cactorum (*Phytophthora cactorum*), susceptible to *Verticillium.*

Weather tolerance: tolerant to low and high temperatures and little susceptible to rain damage.

Foliage:

*Arrangement* (*e.g., alternate, single*).—Rosette.

*Number of leaves per stem.*—3.

*Whole leaf length.*—Approximately 11.5 cm.

*Whole leaf width.*—Approximately 19 cm.

*Rugosity.*—Strong.

*Glossiness.*—Weak.

*Petiole.*—Length: Approximately 14 cm. Diameter: Approximately 3 mm. Color: light green; Strong Yellow Green RHS 144B. Texture: hairy to smooth.

*Stipule.*—Average number per leaf: 2. Length: Approximately 4 cm. Width: Approximately 3 cm. Color: pale green; Strong Yellow Green RHS 144B-144C.

*Color.*—Young leaflets: Upper surface: dark green; Dark Yellowish Green RHS 139A. Lower surface: (light) green; Moderate Yellow Green RHS 138B. Mature leaflets: Upper surface: (dark) green; Moderate Olive Green RHS 137A. Lower surface: (light) green; Moderate Yellow Green RHS 138B.

Lateral leaflets:

*Length.*—Approximately 9.5 cm.

*Width.*—Approximately 11 cm.

*Shape of leaf* (*generally*).—Rounded.

*Shape of apex.*—Rounded.

*Shape of base.*—Obtused.

*Texture* (*both surfaces*).—Rough, medium blistering.

*Aspect.*—Approximately 120-145 degrees.

*Margin type.*—Crenate.

Terminal leaflets:

*Length.*—Approximately 10 cm.

*Width.*—Approximately 9.5 cm.

*Shape of leaf* (*generally*).—Rounded.

*Shape of apex.*—Rounded.

*Shape of base.*—Obtused.

*Texture* (*both surfaces*).—Rough, medium blistering.

*Aspect.*—Approximately 180 degrees.

*Margin type.*—Crenate.

Veins:

*Venation pattern.*—Netted veins or reticulate venation.

*Color.*—Upper surface: (light) green; Moderate Yellow Green RHS 138B. Lower surface: (light) green; Moderate Yellow Green RHS 138B.

Fruit:

*Harvest season.*—End of December to beginning of June.

*Number of fruit per fruiting lateral.*—1 to 2.

*Color.*—Immature: light green; Light Yellow Green RHS 145C. Maturing: light orange-red; Vivid Reddish Orange RHS 44C. Fully mature: medium red; Vivid Red RHS 44A. Evenness of color: even.

*Taste.*—Sweet with rich aroma.

*Length.*—Approximately 7 cm.

*Width.*—Approximately 4.7 cm.

*Length/width ratio.*—Approximately 1.49.

*Overall shape.*—Ovoid to rhomboid.

*Glossiness.*—Medium.

*Weight.*—25 to 30 grams.

*Achene position.*—Sunken/(strongly) below surface.

*Achene color.*—Yellow to light green; Strong Greenish Yellow RHS 153C.

*Average number of achenes per berry.*—220-270.

*Flesh firmness.*—Somewhat weak.

*Fruiting truss length.*—12-18 cm.

*Fruiting truss width.*—Approximately 3 mm.

*Fruiting truss color.*—Yellow Green RHS N144D and RHS 144C.

Reproductive organs:

*Stamens.*—Number per flower: Approximately 20. Length: 2-5 mm. Width: Approximately 1 mm.

*Anthers.*—Apex shape: rounded. Base Shape: split. Length: Approximately 1.5 mm. Width: Approximately 0.5 mm. Color: Edge: light yellow; Strong Greenish Yellow RHS 153C. Center: light yellow; Strong Greenish Yellow RHS 153C.

*Stigma.*—Shape: round open. Color: yellowish; Strong Yellow RHS 153D.

*Style.*—Length: Approximately 1.5 mm. Color: pale white; Brilliant Greenish Yellow RHS 151D.

*Ovary.*—Texture: grainy. Length: Approximately 7 mm. Color (with and without seed): with seeds light green; Strong Greenish Yellow RHS 151C; without seeds almost white; Light Yellow Green 150D.

*Stolon.*—Length: Mother plant to first stolon-plant: Approximately 35 cm. Mother plant to second stolon-plant: Approximately 60 cm. Diameter: 4-5 mm. Color: light green, same as petiole; Strong Yellow Green RHS 144B.

Flowers:

*Natural flowering season at specified location*(*s*).—from end of November until mid-May.

*Number of flowers per plant.*—Approximately 45.

*Fragrance.*—Absent.

*Longevity.*—About one week.

*Flower type.*—Saucer.

*Flower height.*—Approximately 1 cm.

*Flower diameter.*—Approximately 3 cm.

*Inflorescence location.*—Slightly below to same level as the foliage.

*Petal.*—Number per flower: 5-6. Shape: round/circular. Arrangement: Overlapping. Length: Approximately 1.2 cm. Width: Approximately 1.5 cm. Apex: round. Base: obtuse. Margin: smooth. Texture (both surfaces): both surfaces are soft. Color: Mature petal: Upper surface: pale yellow/white; Pale Yellow Green RHS 4D. Lower surface: pale yellow/white; Pale Yellow Green RHS 4D. Young petal: Upper surface: pale yellow/white; Pale Yellow Green RHS 4D. Lower surface: pale yellow/white; Pale Yellow Green RHS 4D.

*Sepals.*—Number per flower: 10-12. Length: Approximately 2 cm. Width: Approximately 1 cm. Shape:

elliptical. Attitude: Upwards. Apex: pointed to divided. Margin: sometimes serrate. Texture: smooth. Color: Mature sepal: Upper surface: dark green; Dark Yellowish Green RHS 139A. Lower surface: light green; Moderate Yellowish Green RHS 138A. Young sepal: Upper surface: dark green; Dark Yellowish Green RHS 139A. Lower surface: light green; Moderate Yellowish Green RHS 138A.

*Buds*.—Length: Approximately 2 cm. Diameter: Approximately 1 cm. Shape: oval. Color: light green (same as petiole); Strong Yellowish Green RHS 144B.

*Calyx*.—Diameter in relation to the diameter of the fruit: Slightly larger. However, since the calyx is folded upwards, it may appear to be smaller. Size in relation to corolla: Larger. Position of attachment of the fruit: Raised.

*Flowering runners*.—Absent.

I claim:

1. A new and distinct variety of strawberry plant named 'BACHATA', as is herein illustrated and described.

* * * * *